(12) United States Patent
Hense

(10) Patent No.: US 7,444,699 B2
(45) Date of Patent: *Nov. 4, 2008

(54) INFLATABLE KNEE PILLOW HAVING THIN PROFILE AND FOLDABILITY WHEN DEFLATED

(75) Inventor: Matthaus Hense, San Mateo, CA (US)

(73) Assignees: William B. Jackson, San Mateo, CA (US); Lisa A. Jackson, San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/869,232

(22) Filed: Oct. 9, 2007

(65) Prior Publication Data

US 2008/0028531 A1    Feb. 7, 2008

Related U.S. Application Data

(62) Division of application No. 11/331,915, filed on Jan. 13, 2006, now Pat. No. 7,296,313.

(51) Int. Cl.
*A47C 16/02* (2006.01)
*A61F 5/37* (2006.01)

(52) U.S. Cl. .............................. 5/648; 5/655.3; 5/657; 5/660; 128/882

(58) Field of Classification Search ............... 5/648, 5/650, 655.3, 644, 657, 640; 2/24; 128/882, 128/892, 894
See application file for complete search history.

(56) References Cited

U.S. PATENT DOCUMENTS

| | | | |
|---|---|---|---|
| 2,522,120 A | 9/1950 | Kaskey et al. | 5/337 |
| 3,312,987 A | 4/1967 | Emery | 5/337 |
| 3,593,340 A | 7/1971 | Powell | 2/24 |
| 4,060,863 A | 12/1977 | Craig | 5/337 |
| 4,120,052 A | 10/1978 | Butler | 2/16 |
| 4,177,806 A | 12/1979 | Griffin | 128/132 R |
| 4,371,985 A * | 2/1983 | Pokhis | 2/22 |
| 4,706,302 A | 11/1987 | Padfield et al. | 2/22 |
| 4,736,477 A | 4/1988 | Moore | 5/443 |
| 4,889,109 A | 12/1989 | Gifford | 128/80 |
| 5,117,522 A | 6/1992 | Everett | 5/648 |
| 5,451,201 A | 9/1995 | Prengler | 602/26 |
| 5,544,378 A | 8/1996 | Chow | 5/644 |
| 5,560,041 A | 10/1996 | Walker | 2/24 |
| 5,613,941 A | 3/1997 | Prengler | 602/13 |
| 6,145,508 A | 11/2000 | Seip, Jr. | 128/845 |

(Continued)

*Primary Examiner*—Michael Trettel
(74) *Attorney, Agent, or Firm*—Girard & Equitz LLP

(57) ABSTRACT

In some embodiments, an inflatable knee pillow including a body having an outer fabric surface, and an inflation valve, wherein the body defines straps (preferably two pairs of straps) and encloses a bladder (an inflatable volume), and the inflation valve is in fluid communication with the bladder. When deflated, the pillow has a thin profile and can be folded into a compact configuration. The straps are releasably fastenable around a user's leg so as to position an inflatable portion of the pillow against the inside of the user's knee (for example, to cushion and separate the user's knees from each other while the user sleeps on his or her side with the pillow inflated). Preferably, the body includes two sheets of multilayer material shaped and attached together so as to define the straps and the bladder, and the pillow has releasable fasteners (e.g., hook-and-loop fasteners) defined by or attached to the straps.

9 Claims, 1 Drawing Sheet

U.S. PATENT DOCUMENTS

| | | | |
|---|---|---|---|
| 6,182,311 B1 | 2/2001 | Buchanan et al. | 5/632 |
| 6,438,779 B1 | 8/2002 | Brown | 5/648 |
| 6,637,059 B1 | 10/2003 | Baker | 5/644 |
| 6,748,615 B1 * | 6/2004 | Tiedemann | 5/640 |
| 6,807,697 B2 | 10/2004 | Druery et al. | 5/650 |
| 6,954,953 B2 | 10/2005 | Bordan | 5/648 |
| 6,957,462 B1 * | 10/2005 | Wilcox | 5/636 |
| 2003/0005521 A1 | 1/2003 | Sramek | 5/648 |

* cited by examiner

INFLATABLE KNEE PILLOW HAVING THIN PROFILE AND FOLDABILITY WHEN DEFLATED

CROSS-REFERENCE TO RELATED APPLICATION

This application is a divisional of U.S. patent application Ser. No. 11/331,915, entitled "Inflatable Knee Pillow Having Thin Profile and Foldability When Deflated," by M. Hense, filed on Jan. 13, 2006 and now U.S. Pat. No. 7,296,313.

FIELD OF THE INVENTION

The present invention relates to an inflatable pillow designed to be releasably fastened to a user's leg with an inflatable portion against the inside of the user's knee (e.g., for cushioning the user's knees while the user sleeps). In preferred embodiments, the inventive knee pillow has a thin profile and can be folded into a compact configuration (e.g., into a small and compact package) when not inflated.

BACKGROUND OF THE INVENTION

Knee pillows having a variety of shapes and structures have been proposed for cushioning the knees of the user. Some such pillows are intended to be positioned between the user's knees (e.g., while the user sleeps on his or her side) to prevent one knee from exerting painful or uncomfortable pressure on the other. Such knee pressure may be especially painful or uncomfortable to some users, for example some persons having an arthritic condition in their lower extremities.

Some knee pillows are designed to be strapped to one or both legs of the user by straps, in a position for separating and cushioning the user's knees (e.g., while the user sleeps on his or her side). For example, U.S. Pat. No. 4,177,806, issued Dec. 11, 1979, discloses a knee pillow including a cloth-covered resilient pad with one or two pairs of straps to be fastened to at least one leg of a user; U.S. Pat. No. 4,736,477, issued Apr. 12, 1988, discloses a knee pillow including a plastic-covered (or cloth-covered), deformable and resilient core with straps to be fastened to a user's leg; U.S. Pat. No. 6,145,508, issued Nov. 14, 2000, discloses a knee pillow including three cloth-covered cushions (two made of foam, gel, down, or other "first" cushion material; the other made of batting or other material different than the first cushion material) and straps having releasable fasteners (e.g., hook-and-loop fasteners) to be fastened to a user's leg; U.S. Pat. No. 4,706,302, issued Nov. 17, 1987, discloses a knee pad having a Y-shaped strap (with hook and loop fasteners to be fastened to a user's leg) and a pad that can include padding, liquid gel, or other cushioning material; and U.S. Pat. No. 6,807,697, issued Oct. 26, 2004, discloses a knee pillow with three straps having hook and loop fasteners, and a covered pad filled with resilient material (e.g., a pad filled with polyurethane foam and covered by a washable cover). Similarly, U.S. Pat. No. 5,560,041, issued Oct. 1, 1996, discloses an equestrian knee grip-pad having two straps with hook and loop fasteners and a pad having a high-friction outer surface and low-friction inner surface. However, the pillows and pads disclosed in the cited references are bulky and typically, undesirably heavy, because they are filled with resilient or other cushioning material.

U.S. Pat. No. 4,889,109, issued Dec. 26, 1989, discloses a large knee pillow having complicated shape and a strap for surrounding both legs of the user. The pillow has a central projecting portion to be placed between the user's knees to separate the knees while the legs of a user in a supine position rest on end portions of the pillow. An inflatable embodiment of this pillow (shown in FIG. 7 of U.S. Pat. No. 4,889,109) is also undesirably large with an undesirably complicated shape and design (including a central projecting portion to be placed between the knees of a supine user while the user's legs rest on end portions of the pillow, and internal structural members for holding the pillow in its intended inflated shape), and is unsuitable for use by a user lying on his or her side.

U.S. Pat. No. 5,613,941, issued Mar. 25, 1997, and U.S. Pat. No. 5,451,201, issued Sep. 19, 1995, disclose knee supports (braces) for restricting movement of the knee joint. One such support is filled with resilient material and has two straps to be fastened to a user's leg; another has two such straps, a resilient body, and an inflatable bladder attached to the body. The bladder has a generally circular or oval central portion for encircling the user's patella and two elongated stay portions for lateral support. These knee supports are heavy and bulky, and unsuitable for use as knee pillows.

There is a need for an inflatable knee pillow which is lightweight, inexpensively manufacturable, comfortable to wear (over clothing or against bare skin), provides good knee cushioning (e.g., to a user lying on his or her side), and is easily inflatable (e.g., without use of an air pump), and also has a thin profile when not inflated and can be folded into a small package when not inflated.

SUMMARY OF THE INVENTION

In a class of embodiments, the invention is an inflatable knee pillow comprising a body having an outer fabric surface (an outer surface made of fabric), and an inflation valve (e.g., an air check valve). The body defines straps (preferably two pairs of straps) and encloses an inflatable volume (bladder), and the inflation valve is in fluid communication with the bladder. When deflated, the pillow has a thin profile and can be folded into a compact configuration. The straps can be releasably fastened around a user's leg so as to position an inflatable portion of the pillow against the inside of the user's knee (e.g., for cushioning and separating the user's knees from each other while the user sleeps on his or her side with the pillow inflated).

Preferably, the body comprises two sheets of multilayer material shaped and attached (e.g., bonded, welded, or attached by glue or another adhesive) together so as to define the straps and bladder, and the pillow includes releasable fasteners defined by or attached to the straps (e.g., hook-and-loop fasteners attached to outer surfaces of the straps). Preferably, each multilayer sheet has an impermeable layer (a layer of plastic or other material impermeable to air or other inflating fluid) and a fabric layer (preferably adhered directly to the impermeable layer, but alternatively adhered to an intermediate layer between the impermeable layer and the fabric layer). Preferably, the sheets are attached together with their fabric layers exposed to define the pillow's outer surface and their impermeable layers enclosed between the fabric layers to define at least a portion of the bladder.

Preferably, the bladder has a generally rectangular shape. For example, in some embodiments in which the pillow comprises two multilayer sheets, the sheets are aligned and attached to each other at a rectangular seam at (or near to) their aligned outer peripheries.

Preferably, the pillow's outer edges define the outer edges of two pairs of elongated straps, and smooth (straight or curved) edge portions between each two adjacent straps (so that a user is not exposed to any sharp edge portion when the pillow is strapped to the user's leg). Preferably, the straps in one pair are aligned with each other along a first axis, and the straps in the other pair are aligned with each other along a second axis that is at least substantially parallel to the first axis.

Preferably, the pillow is implemented to be lightweight (e.g., weighs no more than about 2 ounces) and its exposed outer fabric surface consists of fabric that is comfortable to wear (either over clothing or against the user's bare skin), does not absorb significant amounts of water or bodily fluids, and is easily cleanable. Preferably, the pillow's inflated thickness is variable in accordance with the user's need and preference, depending on the amount of air (or other inflating fluid) that the user introduces into the bladder during inflation, and its maximum inflated thickness in the range from three to four inches (e.g., it is at least substantially equal to 3.5 inches).

Preferably, no pump is required to inflate the pillow (a user can instead blow into the inflation valve to inflate the pillow) and the inflated pillow is easily deflated (e.g., by squeezing a flexible inflation valve to release the inflating fluid from the bladder).

DETAILED DESCRIPTION OF THE INVENTION

The term "bladder" herein denotes an inflatable volume.

An embodiment of the inventive knee pillow will be described with reference to FIGS. 1 and 3. A multilayer sheet that can be used to manufacture the pillow of FIG. 1 and other embodiments of the invention will be described with reference to FIG. 2.

Figure 1:
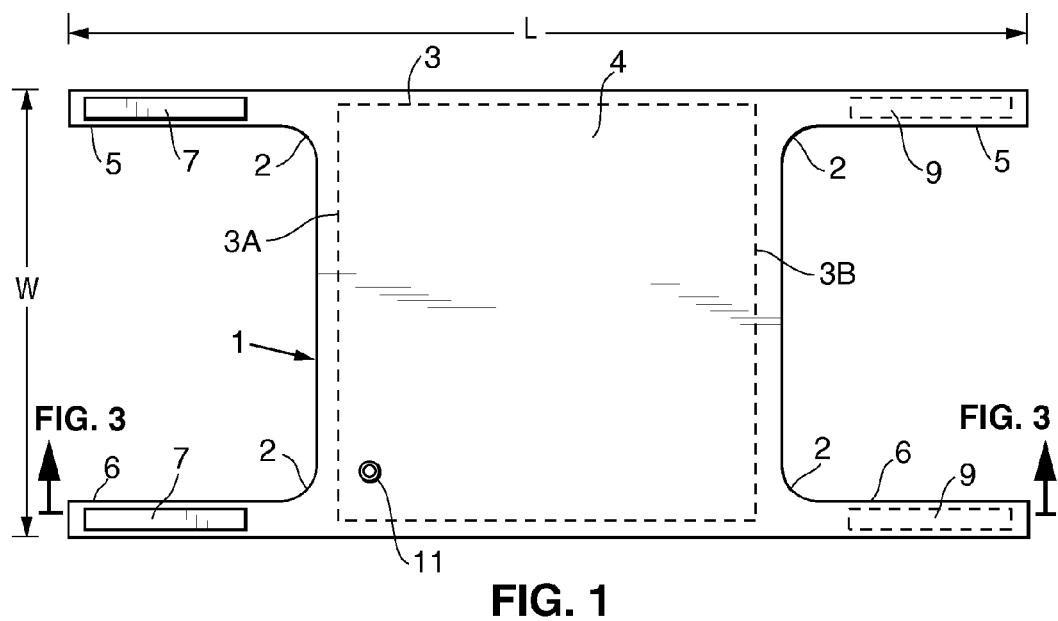
FIG. 1 is an top view of an embodiment of the inventive knee pillow.

Inflatable knee pillow 1 of FIG. 1 has an outer surface made of fabric, a first pair of straps 5, a second pair of straps 6, and an inflation valve 11 (which can be an air check valve). The outer fabric surface encloses bladder 4. More specifically, pillow 1 comprises two sheets 20 (shown in FIG. 3) attached to each other at seam 3. Seam 3 (which includes opposed seam portions 3A and 3B) is rectangular, and thus defines a rectangular outer edge of bladder 4.

In alternative embodiments, the bladder of the inventive pillow has a generally rectangular (but not exactly rectangular) shape or another shape.

The surfaces of sheets 20 that face each other can be attached (e.g., bonded, welded, or attached by glue or another adhesive) together everywhere (including at the portions that define straps 5 and 6) except at the areas above and below bladder 4. For example, seam 3 can be the inner surfaces of a volume of adhesive material 12 as shown in FIG. 3, so that bladder 4 is the volume enclosed by sheets 20 and adhesive material 12.

Straps 5 and 6 are elongated portions of sheets 20. Hook-and-loop fasteners (e.g., Velcro fasteners) are attached to outer surfaces of straps 5 and 6, with hook portion 7 of a first hook-and-loop fastener attached to the upper outer surface of one of straps 5, loop portion 9 of the first hook-and-loop fastener attached to the lower outer surface of the opposing strap 5, hook portion 7 of a second hook-and-loop fastener attached to the upper outer surface of one of straps 6, and loop portion 9 of the second hook-and-loop fastener attached to the opposing strap 6.

In alternative embodiments, other releasable fasteners are defined by (e.g., integrally formed with), or attached to, the straps of the inventive pillow. For example, the body of the inventive pillow can comprise two multilayer sheets (attached together to define and enclose a bladder and to define straps), at least a portion of at least one strap portion of one sheet has an outer fabric layer consisting of hook material (of a hook-and-loop fastener), and at least a portion of at least one strap portion of the other sheet has an outer fabric layer consisting of loop material (of a hook-and-loop fastener).

Figure 3:
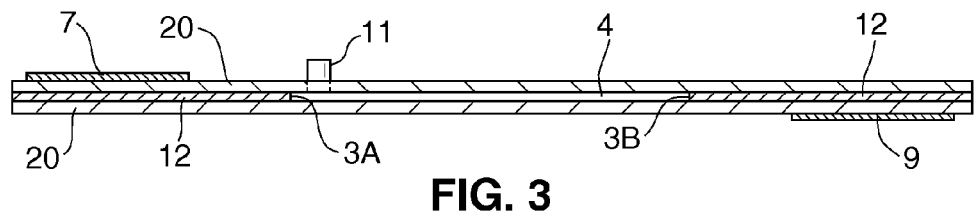
FIG. 3 is a side elevational view of an implementation of the pillow of FIG. 1, showing that the pillow comprises two sheets (20), each of which can be a multilayer sheet of the type shown in FIG. 2.

As shown in FIG. 3, the inner end of inflation valve 11 is in fluid communication with bladder 4. A user can blow air into the outer end of valve 11 to inflate bladder 4.

Figure 2:
FIG. 2 is a side elevational view of one multilayer sheet (30) that can be used to manufacture the pillow of FIG. 1.

Preferably, each sheet 20 of pillow 1 is a flexible, multi-layer sheet 30 of the type shown in FIG. 2. Sheet 30 includes impermeable layer 21 (a layer of plastic or other material impermeable to air or other inflating fluid) and fabric layer 22 adhered directly to impermeable layer 21. Alternatively, the body of the inventive pillow can comprise two multilayer sheets, each sheet consisting of at least three layers including at least one intermediate layer between an outer impermeable layer and an outer fabric layer. When two sheets 30 are attached together to form pillow 1, the sheets' impermeable layers 21 are attached together at seam 3, the sheets' fabric layers 22 are exposed to the user to define the pillow's outer surface (except where they are covered by releasable fasteners or removed to define an orifice for receiving an inflation valve), and bladder 4 is defined (i.e., surrounded) by facing portions of impermeable layers 21 and seam 3.

When deflated (as shown in FIG. 3), pillow 1 has a thin profile and can folded into a compact configuration.

Pillow 1 is flexible, and each pair of flexible straps 5 and 6 is configured to be wrapped around a user's leg and releasably fastened together (by fasteners 7 and 9) so as to position bladder 4 against the inside of the user's knee. When pillow 1 is strapped in this way to a user's leg and bladder 4 is inflated, pillow 1 can cushion and separates the user's knees from each other while the user sleeps on his or her side.

As shown in FIG. 1, outer edges of pillow 1 (the edges at the top and bottom of FIG. 1) define outer edges of straps 5 and 6, and edge portions 2 of pillow 1 between straps 5 and 6 at the left side of pillow 1 (and between straps 5 and 6 at the right side of pillow 1) are curved, so as to prevent a user from being exposed to any sharp edge portion when pillow 1 is strapped around a leg of the user.

A first pair of straps 5,6 (at the top of FIG. 1) are aligned with each other along a first axis, and second pair of straps 5,6 (at the bottom of FIG. 1) are aligned with each other along a second axis substantially parallel to the first axis. In alternative embodiments, the inventive pillow has more or less than four straps (e.g., it has two or three straps) and/or its straps are shaped and/or aligned differently than shown in FIG. 1.

Preferably, pillow 1 is implemented to be lightweight (e.g., it weighs no more than about 2 ounces, with a width "W" of about 8.5 inches and a length "L" of about 25 inches in one implementation) and its exposed outer fabric surface consists of fabric that is comfortable to wear (either over clothing or against the user's bare skin), does not absorb significant amounts of water or bodily fluids, and is easily cleanable. Preferably, the inflated thickness (in the direction perpendicular to the plane of FIG. 1) of bladder 4 is variable in accordance with the user's need and preference, depending on the amount of air (or other inflating fluid) that the user introduces into the bladder during inflation, and its maximum inflated thickness is in the range from about three to about four inches (e.g., it is equal to about 3.5 inches).

Preferably, no pump is required to inflate pillow 1. Preferably, a user can instead blow into inflation valve 11 to inflate bladder 4, and inflated pillow 1 is easily deflated (e.g., by squeezing a flexible plastic implementation of inflation valve 11 to release the inflating fluid from bladder 4).

While this invention has been described in terms certain preferred embodiments, it will be appreciated by those skilled in the art that certain modifications, permutations and equivalents thereof are within the inventive scope of the present invention. It is therefore intended that the following appended claims include all such modifications, permutations and equivalents as fall within the true spirit and scope of the present invention.

What is claimed is:

1. An inflatable knee pillow configured to be releasably fastened around a user's leg so as to position an inflatable portion of the pillow against the inside of the user's knee, said pillow comprising:
    a body having an outer fabric surface; and
    an inflation valve, wherein the body defines straps and encloses a bladder, the straps are releasably fastenable around the user's leg so as to position an inflatable portion of the pillow against the user's knee, the inflation valve is in fluid communication with the bladder, and when deflated, the pillow has a thin profile and can be folded into a compact configuration, and wherein said pillow has a variable inflated thickness, the bladder is inflatable by introducing inflating fluid through the inflation valve into the bladder, and the amount of the inflating fluid within the bladder determines the inflated thickness.

2. The pillow of claim 1, wherein the bladder is an inflatable volume having a generally rectangular shape.

3. The pillow of claim 1, wherein the body defines two pairs of elongated straps.

4. The pillow of claim 3, wherein outer edges of the pillow define:
    outer edges of the elongated straps; and
    smooth edge portions between each two adjacent ones of the elongated straps.

5. The pillow of claim 3, wherein the straps in one of the pairs of elongated straps are aligned with each other along a first axis, and the straps in the other one of the pairs of elongated straps are aligned with each other along a second axis that is at least substantially parallel to the first axis.

6. The pillow of claim 1, wherein the body comprises two sheets of multilayer material shaped and attached together so as to define the straps and the bladder, and wherein the pillow includes releasable fasteners attached to outer surfaces of at least some of the straps.

7. The pillow of claim 6, wherein the releasable fasteners are hook-and-loop fasteners.

8. The pillow of claim 1, wherein the body comprises two sheets of multilayer material shaped and attached together so as to define the straps and the bladder, and wherein the straps define releasable fasteners.

9. The pillow of claim 1, wherein the pillow has a maximum inflated thickness in a range from three inches to four inches.

* * * * *